United States Patent
Umezu et al.

(10) Patent No.: US 6,197,969 B1
(45) Date of Patent: Mar. 6, 2001

(54) PROCESS FOR PRODUCING SUBSTITUTED ALKYLAMINES OR SALTS THEREOF

(75) Inventors: Kazuto Umezu; Shuji Taniguchi; Mahito Ogawa; Hidetaka Hiyoshi, all of Shizuoka (JP)

(73) Assignee: Ihara Chemical Industry Co., LTD., Tokyo (JP)

( * ) Notice: Subject to any disclaimer, the term of this patent is extended or adjusted under 35 U.S.C. 154(b) by 0 days.

(21) Appl. No.: 09/509,783
(22) PCT Filed: Sep. 24, 1998
(86) PCT No.: PCT/JP98/04284
  § 371 Date: Apr. 3, 2000
  § 102(e) Date: Apr. 3, 2000
(87) PCT Pub. No.: WO99/16759
  PCT Pub. Date: Apr. 8, 1999

(30) Foreign Application Priority Data
  Oct. 1, 1997 (JP) .................................... 9-284337

(51) Int. Cl.$^7$ ................................. C07D 277/64
(52) U.S. Cl. ............................................ 548/152
(58) Field of Search .............................. 548/152

(56) References Cited

U.S. PATENT DOCUMENTS 4,000,079 * 12/1976 Rasp et al. ............................. 252/75
4,425,338    1/1984 Huang ................................... 424/200

FOREIGN PATENT DOCUMENTS 8-325235  12/1996  (JP).

OTHER PUBLICATIONS

"Morrison & Boyd: Organic Chemistry (vol. 2) 6th ed. (in Japanese)", translated by Koji Nakanishi et al., 6th ed., 2nd printing, 1995, p.1040.

* cited by examiner

Primary Examiner—Laura L. Stockton
(74) Attorney, Agent, or Firm—Kubovcik & Kubovcik

(57) ABSTRACT

The present invention provides a process for producing a substituted alkylamine represented by formula (3):

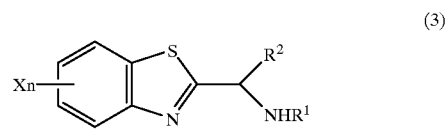

(3)

or a salt thereof, which process comprises reacting a 2-aminothiophenol derivative metal salt represented by formula (1):

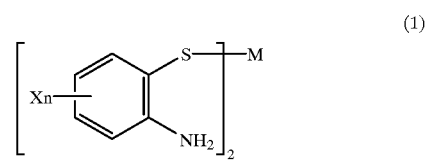

(1)

with an amino acid-N-carboxy anhydride represented by formula (2):

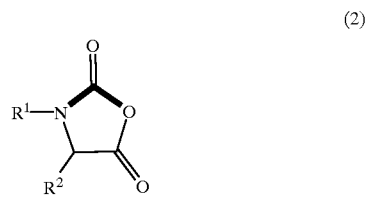

(2)

and then subjecting the reaction product to cyclization under an acidic condition. A substituted alkylamine typified by 1-(2-benzothioazolyl)akylamine, or a salt thereof can be produced from a 2-aminothiophenol derivative industrially at a high handleability and a high yield, and even when the intended substituted alkylamine is an optically active compound, the intended product can be produced without reducing the optical purity of the optically active raw material.

16 Claims, No Drawings

PROCESS FOR PRODUCING SUBSTITUTED ALKYLAMINES OR SALTS THEREOF

This application is a 371 of PCT/JP98/04284 filed Sep. 24, 1998.

TECHNICAL FIELD

The present invention relates to a process for producing a substituted alkylamine having a condensed heterocyclic ring or its salt, which is useful as an intermediate for medicines and agricultural chemicals.

BACKGROUND ART

As a substituted alkylamine having a condensed heterocyclic ring, useful for the above usage, there are known 1-(2-benzothiazolyl)alkylamines represented by the following formula:

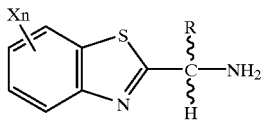

For synthesis thereof, a process is known which uses a condensation reaction between 2-aminothiophenol derivative and amino acid-N-carboxy anhydride (see JP-A-8-325235).

However, for example, (RS)-1-(6-fluoro-2-benzothiazolyl)ethylamine produced by the above conventional process is low (34%) in yield; moreover, the 2-aminothiophenol derivative used as a raw material is unstable in air and emits an odor and, therefore, has been difficult to handle industrially.

Thus, there has been proposed no industrial process capable of synthesizing a 1-(2-benzothiazolyl)alkylamine from a 2-aminothiophenol derivative at a high yield with easy handling of the derivative.

In view of such a situation of the prior art, the present invention has been completed with an aim of providing an industrial process capable of synthesizing a 1-(2-benzothiazolyl)alkylamine or its salt from a 2-aminothiophenol derivative at a high yield with easy handling of the derivative.

DISCLOSURE OF THE INVENTION

The present inventors surprisingly found out that by using a 2-aminothiophenol derivative metal salt, which is stable in air, emits no odor and accordingly is easy in industrial handling, and by reacting it with an amino acid-N-carboxy anhydride and then cyclizing the reaction product in an acidic condition, a 1-(2-benzothiazolyl)alkylamine or its salt can be obtained at a high yield. A further study by the present inventors has led to the completion of the present invention.

In the present invention, the above aim has been achieved by providing the following inventions [1] to [10]:

[1] A process for producing a substituted alkylamine represented by the following general formula (3):

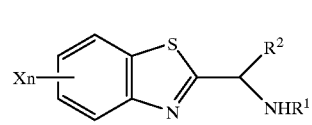

(wherein X is a hydrogen atom, a halogen atom, an alkyl group, an alkoxy group, a cyano group or a nitro group; n is an integer of 1 to 4; and $R^1$ and $R^2$ are each independently a hydrogen atom or an alkyl group which may be substituted with phenyl group, and may together form a 5- or 6-membered ring) or a salt thereof, which process comprises reacting a 2-aminothiophenol derivative metal salt represented by the following general formula (1):

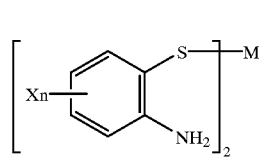

(wherein M is a bivalent metal atom; X has the same definition as given above; and n has the same definition as given above) with an amino acid-N-carboxy anhydride represented by the following general formula (2):

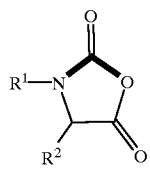

(wherein $R^1$ and $R^2$ have the same definitions as given above) and then subjecting the reaction product to cyclization under an acidic condition.

[2] A process for producing a substituted alkylamine or a salt thereof, set forth in [1], wherein the reaction of the 2-aminothiophenol derivative metal salt represented by the general formula (1) with the amino acid-N-carboxy anhydride represented by the general formula (2) is conducted in an amide type aprotic polar solvent.

[3] A process for producing a substituted alkylamine or a salt thereof, set forth in [1] or [2], wherein the 2-aminothiophenol derivative metal salt represented by the general formula (1) is a salt of a Ib or IIb group metal.

[4] A process for producing a substituted alkylamine or a salt thereof, set forth in [3], wherein the 2-A aminothiophenol derivative metal salt represented by the general formula (1) is a zinc salt.

[5] A process for producing a substituted alkylamine or a salt thereof, set forth in [1] or [2], wherein the amino acid-N-carboxy anhydride represented by the formula (2) is DL-alanine-N-carboxy anhydride, D-alanine-N-carboxy anhydride or L-alanine-N-carboxy anhydride.

[6] A process for producing a substituted alkylamine or a salt thereof, set forth in [1] or [2], wherein the reaction of the 2-aminothiophenol derivative metal salt represented by the general formula (1) with the amino acid-N-carboxy anhydride represented by the general formula (2) is conducted in a temperature range of −50 to 60° C.

[7] A process for producing a substituted alkylamine or a salt thereof, set forth in [1] or [2], wherein the reaction of the 2-aminothiophenol derivative metal salt represented by the general formula (1) with the amino acid-N-carboxy anhydride represented by the general formula (2) is conducted in a temperature range of −30 to 10° C.

[8] A (substituted) benzenesulfonic acid salt of a 1-(6-halogeno-2-benzothiazolyl)ethylamine represented by the following formula:

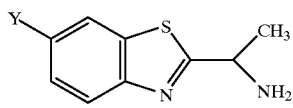

(wherein Y is a halogen atom).

[9] A (substituted) benzenesulfonic acid salt set forth in [8], wherein the (substituted) benzenesulfonic acid is p-toluenesulfonic acid.

10. A (substituted) benzenesulfonic acid salt set forth in [8] or [9], wherein Y is a fluorine atom.

The (substituted) benzenesulfonic acid salt of a 1-(6-halogeno-2-benzothiazolyl)ethylamine set forth in [8] to [10] includes a pure optical isomer of R-configuration, a pure optical isomer of S-configuration, a racemic modification and a mixture of any proportions of different optically active compounds (R-configuration and S-configuration).

BEST MODE FOR CARRYING OUT THE INVENTION

The present invention is described in detail below.

In the process of the present invention, first, a 2-aminothiophenol derivative metal salt represented by the following general formula (1):

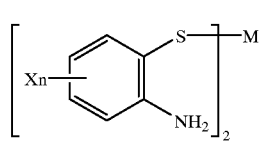

(1)

is reacted with an amino acid-N-carboxy anhydride represented by the general formula (2).

The 2-aminothiophenol derivative metal salt used as a raw material in the above reaction may be any compound represented by the general formula (1) and has no other restriction. In the formula, M is a bivalent metal atom, and the metal atom can be exemplified by atoms of bivalent transition metals or alkaline earth metals such as zinc, copper, nickel, magnesium, calcium and the like. A Ib or IIb group metal is preferred, and zinc is particularly preferred.

In the formula (1), X is a hydrogen atom; a halogen atom including chlorine, fluorine, bromine or iodine; a straight chain or branched chain alkyl group having 1 to 6 carbon atoms, including methyl group, ethyl group, n-propyl group, isopropyl group, n-butyl group, isobutyl group, sec-butyl group, tert-butyl group, n-pentyl group, n-hexyl group or the like; an alkoxy group (—O-alkyl group) whose alkyl moiety is the above-mentioned alkyl group; a cyano group; or a nitro group. The site(s) to which X bonds, is (are) not restricted; and n is an integer of 1 to 4 and refers to the number of X bonding to the aromatic ring of the formula (1).

As the 2-aminothiophenol derivative metal salt represented by the general formula (1) having the above-mentioned M, X and n, which can be used as a raw material in the above reaction, there can be mentioned, for example, bis(2-aminothiophenol) zinc salt, bis(6-fluoro-2-aminothiophenol) zinc salt, bis(6-chloro-2-aminothiophenol) zinc salt, bis(5-fluoro-2-aminothiophenol) zinc salt, bis(5-fluoro-2-aminothiophenol) copper salt, bis(5-fluoro-2-aminothiophenol) nickel salt, bis(5-fluoro-2-aminothiophenol) magnesium salt, bis(5-fluoro-2-aminothiophenol) calcium salt, bis(5-bromo-2-aminothiophenol) zinc salt, bis(5-chloro-2-aminothiophenol) zinc salt, bis(5-methyl-2-aminothiophenol) zinc salt, bis(5-methoxy-2-aminothiophenol) zinc salt, bis(4-fluoro-2-aminothiophenol) zinc salt, bis(4-chloro-2-aminothiophenol) zinc salt, bis(4-cyano-2-aminothiophenol) zinc salt, bis(4-nitro-2-aminothiophenol) zinc salt, bis(4-methyl-2-aminothiophenol) zinc salt, bis(4,5-difluoro-2-aminothiophenol) zinc salt, bis(3-fluoro-2-aminothiophenol) zinc salt, bis(3-bromo-2-aminothiophenol) zinc salt, bis(3-chloro-2-aminothiophenol) zinc salt, and bis(3-methyl-2-aminothiophenol) zinc salt. Industrially, a zinc salt is most ordinary and preferred in view of the yield.

There is no restriction, either, as to the method for obtaining the 2-aminothiophenol derivative metal salt represented by the general formula (1). The 2-aminothiophenol derivative metal salt can be produced easily at a high yield according to, for example, the method described in JP-A-6-145158, by hydrolyzing a corresponding 2-aminobenzothiazole derivative with potassium hydroxide and then reacting the hydrolyzate with a metal salt as shown in the following reaction formula:

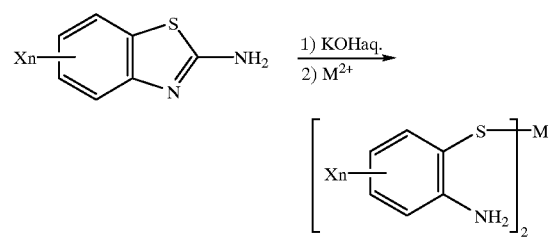

(wherein M, X and n have the same definitions as given above).

The amino acid-N-carboxy anhydride represented by the following general formula (2), which is used as another raw material in the reaction:

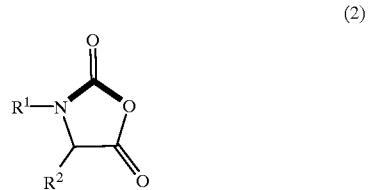

(2)

may be any compound represented by the general formula (2) and has no other restriction. In the compound represented by the general formula (2), the amino acid moiety may be an optically active compound, a mixture of different optically active compounds at any proportions, or a racemic modification. The substituted alkylamine obtained by the present process has the same stereostructure and optical purity as the amino acid used as a starting material in production of the amino acid-N-carboxy anhydride represented by the general formula (2).

In the formula (2), $R^1$ and $R^2$ are each independently a hydrogen atom or an alkyl group, which may be substituted with a phenyl group. The alkyl group can be a straight chain or branched chain alkyl group having 1 to 6 carbon atoms, and specific examples thereof are methyl group, ethyl group, n-propyl group, isopropyl group, n-butyl group, isobutyl group, sec-butyl group, tert-butyl group, n-pentyl group and n-hexyl group. $R^1$ and $R^2$ may together become a triethylene group, a tetraethylene group or the like and, together with the amino acid skeleton, may form a 5- to 6-membered ring.

As the amino acid-N-carboxy anhydride represented by the general formula (2) having the above-mentioned $R^1$ and $R^2$, which can be used as a raw material in the above reaction, there can be mentioned, for example, glycine-N-carboxy anhydride, DL-alanine-N-carboxy anhydride, D-alanine-N-carboxy anhydride, L-alanine-N-carboxy anhydride, DL-valine-N-carboxy anhydride, D-valine-N-carboxy anhydride, L-valine-N-carboxy anhydride, DL-phenylalanine-N-carboxy anhydride, D-phenylalanine-N-carboxy anhydride, L-phenylalanine-N-carboxy anhydride, DL-phenylglycine-N-carboxy anhydride, D-phenylglycine-N-carboxy anhydride, L-phenylglycine-N-carboxy anhydride, DL-proline-N-carboxy anhydride, D-proline-N-carboxy anhydride, L-proline-N-carboxy anhydride, DL-alanine-N-methyl-N-carboxy anhydride, D-alanine-N-methyl-N-carboxy anhydride and L-alanine-N-methyl-N-carboxy anhydride.

The amino acid-N-carboxy anhydride is preferably DL-alanine-N-carboxy anhydride, D-alanine-N-carboxy anhydride or L-alanine-N-carboxy anhydride when the substituted alkylamine or salt thereof obtained by the present invention is used as an intermediate for production of a fungicide for agriculture or horticulture as described later.

There is no particular restriction, either, as to the method for obtaining the amino acid-N-carboxy anhydride represented by the general formula (2). The amino acid-N-carboxy anhydride can be easily produced, for example, according to the method described in J. Org. Chem., Vol. 53, p. 836 (1988), by reacting a corresponding amino acid derivative with phosgene.

In the reaction of the 2-aminothiophenol derivative metal salt with the amino acid-N-carboxy anhydride, the use amount of the amino acid-N-carboxy anhydride represented by the general formula (2) is preferably 2.0 to 2.6 moles per mole of the 2-aminothiophenol derivative metal salt represented by the general formula (1). In this case, the amino acid-N-carboxy anhydride used may be in a dried state or in a state wetted with, for example, a reaction solvent (e.g. tetrahydrofuran) used in the production or an organic solvent used during the recrystallization.

The solvent used in the above reaction can be an aprotic polar solvent. It can be any solvent as long as it is an aprotic polar solvent which can dissolve the 2-aminothiophenol derivative metal salt represented by the general formula (1) and which does not react with the amino acid-N-carboxy anhydride. Specific examples of such a solvent include amide type aprotic polar solvents such as N,N-dimethylformamide, N,N-dimethylacetamide, N,N-diethylacetamide, 1,3-dimethyl-2-imidazolidinone, 1-methyl-2-pyrrolidone, 1,3-dimethyl-3,4,5,6-tetrahydro-2 (1H)-pyrimidinone, 1,1,3,3-tetramethylurea and the like; sulfur-containing aprotic polar solvents such as sulfolane, dimethyl sulfoxide and the like; and hexamethylphosphoric triamide. Of these, an amide type aprotic polar solvent is preferably used.

The above solvents may be used singly or in admixture of two or more kinds. When the solvent used has a melting point higher than the reaction temperature, it is preferred that the solvent is mixed with, for example, an amide type aprotic polar solvent so as to become a liquid at the reaction temperature (described later) and is used as such a mixture. The amount of the solvent used is preferably 300 to 20,000 ml per mole of the 2-aminothiophenol derivative metal salt used as a raw material.

Use, in place of the above solvent, of a non-polar or low-polarity solvent (e.g. chlorobenzene) and further use of a phase-transfer catalyst to conduct a two-phase reaction is disadvantageous from the standpoint of yield, and the significance of selecting such a reaction is substantially low (see Comparative Reference Examples 1 and 2).

The temperature of the above reaction is −50 to 60° C., preferably −30 to 10° C. The reaction time is ordinarily 0.5 to 12 hours. The reaction can be conducted at normal pressure by mixing a 2-aminothiophenol derivative metal salt represented by the general formula (1) with a solvent, adding thereto an amino acid-N-carboxy anhydride represented by the general formula (2) at a given temperature, and stirring the mixture. No pressurization is ordinarily required.

In the process of the present invention, a cyclization reaction is conducted after the above reaction. This cyclization reaction can be conducted by adding an acid, an aqueous solution of an acid, or an acid hydrate to the reaction mixture after the reaction between the 2-aminothiophenol derivative metal salt represented by the general formula (1) with the amino acid-N-carboxy anhydride represented by the general formula (2).

As the acid in the cyclization reaction, an inorganic acid or an organic acid can be used. The inorganic acid can be exemplified by hydrochloric acid, sulfuric acid, hydrobromic acid, hydroiodic acid and perchloric acid. The organic acid can be exemplified by (substituted) benzenesulfonic acids such as p-toluenesulfonic acid, p-chlorobenzenesulfonic acid, benzenesulfonic acid, 2,4-dichlorobenzenesulfonic acid and the like; and (substituted) methanesulfonic acids such as methanesulfonic acid, trifluoromethanesulfonic acid and the like.

The amount of the acid used can be 0.5 to 6.0 moles, preferably 2.0 to 5.0 moles, per mole of the 2-aminothiophenol derivative metal salt represented by the general formula (1). When the acid is added to the reaction system in the form of an aqueous solution, the amount of water can be 0 to 5,000 ml, preferably 0 to 1,000 ml, per mole of the 2-aminothiophenol derivative metal salt represented by the general formula (1).

The temperature of the cyclization reaction is −30 to 60° C., preferably −10 to 10° C. The reaction time is ordinarily 0.5 to 6 hours. The reaction can be conducted at normal pressure at a given temperature by adding an acid, an aqueous solution of an acid, or an acid hydrate and stirring the mixture. No pressurization is ordinarily required.

In the process of the present invention, the intended substituted alkylamine is, after the cyclization reaction, in the form of a salt with the acid used in the cyclization reaction. Therefore, the substituted alkylamine may be taken out in the form of a salt by removing the solvent by distillation. Or, it is possible that an aqueous solution of an alkali metal hydroxide (e.g. sodium hydroxide or potassium hydroxide) is added to the reaction mixture after the cyclization reaction to free the amino group of the substituted alkylamine and then extraction with an organic solvent is conducted to isolate a substituted alkylamine of free form.

When the substituted alkylamine salt formed by the acid used in the cyclization reaction has low crystallizability, it is possible that the amino group of substituted alkylamine is freed and then extracted with an organic solvent, after which the substituted alkylamine of free form is converted into a salt form with an acid different from the acid used in the cyclization reaction and the new salt is taken out.

As mentioned previously, the substituted alkylamine obtained by the process of the present invention has the same stereostructure (absolute configuration) and optical purity as the amino acid used as a starting raw material for the amino acid-N-carboxy anhydride represented by the general formula (2). However, when the intended substituted alkylamine is an optically active compound, the intended substituted alkylamine is preferably isolated in its salt form in order to avoid, for example, the reduction in optical purity caused by isomerization in the post-treatment. Isolation in the form of (substituted) benzenesulfonic acid salt (e.g. p-toluenesulfonic acid salt or benzenesulfonic acid salt) of high crystallizability is particularly preferable in view of safety. Therefore, it is advantageous to select, as the acid used in the cyclization reaction, a (substituted) benzenesulfonic acid typified by p-toluenesulfonic acid or benzenesulfonic acid, for the above reason and also from an operational standpoint.

Thus, the substituted alkylamine represented by the following general formula (3):

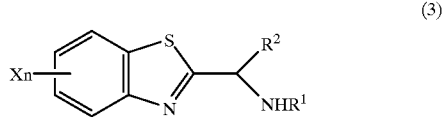

(3)

(wherein X, N, $R^1$ and $R^2$ have the same definitions as given above) or a salt thereof can be produced.

As such a substituted alkylamine, there can be mentioned, for example, (2-benzothiazolyl)methylamine, (6-fluoro-2-benzothiazolyl)methylamine, (RS)-1-(2-benzothiazolyl)ethylamine, (R)-1-(2-benzothiazolyl)ethylamine, (S)-1-(2-benzothiazolyl)ethylamine, (RS)-1-(6-fluoro-2-benzothiazolyl)ethylamine, (R)-1-(6-fluoro-2-benzothiazolyl)ethylamine, (S)-1-(6-fluoro-2-benzothiazolyl)ethylamine, (R)-1-(4-chloro-2-benzothiazolyl)ethylamine, (R)-1-(5-chloro-2-benzothiazolyl)ethylamine, (R)-1-(6-chloro-2-benzothiazolyl)ethylamine, (R)-1-(6-bromo-2-benzothiazolyl)ethylamine, (R)-1-(4-methyl-2-benzothiazolyl)ethylamine, (R)-1-(6-methyl-2-benzothiazolyl)ethylamine, (R)-1-(6-methoxy-2-benzothiazolyl)ethylamine, (R)-1-(5-cyano-2-benzothiazolyl)ethylamine, (R)-1-(5-nitro-2-benzothiazolyl)ethylamine, (RS)-1-(6-fluoro-2-benzothiazolyl)-2-methylporpylamine, (R)-1-(6-fluoro-2-benzothiazolyl)-2-methylpropylamine, (S)-1-(6-fluoro-2-benzothiazolyl)-2 -methylpropylamine, (RS)-1-(4-methyl-2-benzothiazolyl)-2-methylpropylamine, (R)-1-(4-methyl-2-benzothiazolyl)-2-methylpropylamine, (S)-1-(4-methyl-2-benzothiazolyl)-2-methylpropylamine, (RS)-1-(6-fluoro-2-benzothiazolyl)benzylamine, (R)-1-(6-fluoro-2-benzothiazolyl)benzylamine, (S)-21-(6-fluoro-2-benzothiazolyl)benzylamine, (RS)-2-(6-fluoro-2-benzothiazolyl)pyrrolidine, (R)-2-(6-fluoro-2-1benzothiazolyl)pyrrolidine, (S)-2-(6-fluoro-2-benzothiazolyl)pyrrolidine; mineral acid salts thereof such as hydrochloride, sulfate, hydrobromide, hydroiodide, perchloride and the like; and organic acid salts thereof such as p-toluenesulfonate, benzenesulfonate, 2,4-dichlorobenzenesulfonate, methanesulfonate, trifluoromethanesulfonate and the like.

Of these compounds, a (substituted) benzenesulfonate of a 1-(6-halogeno-2-benzothiazolyl)ethylamine represented by the following formula:

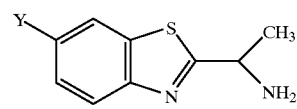

is preferred because it is highly crystallizable as mentioned above; and a p-toluenesulfonate is particularly preferred. In the above formula, Y (which is a halogen atom) is preferably a fluorine atom when the substituted alkylamine is used as an intermediate for production of a fungicide for agriculture or horticulture.

The substituted alkylamine represented by the general formula (3), obtained by the process of the present invention is very useful as an intermediate (described later) for production of a fungicide for agriculture or horticulture (JP-A-8-176115).

Next, the process of the present invention is described more specifically below by way of Examples.

EXAMPLE 1

To 30 ml of N,N-dimethylacetamide, 1.75 g (0.005 mol) of bis(5-fluoro-2-aminothiophenol) zinc salt was added. The mixture was cooled to −10° C. in a nitrogen current. Thereto was added, at the same temperature, 1.14 g (0.01 mol) of D-alanine-N-carboxy anhydride. The mixture was stirred at −13 to −10° C. for 3 hours. Then, thereto was dropwise added, at 5° C. or below, 18 g of a 5% aqueous hydrochloric acid solution. After the completion of the dropwise addition, stirring was conducted at 5° C. or below for 1 hour. The resulting reaction mixture was subjected to high performance liquid chromatography analysis using an absolute calibration method, which indicated a formation of (R)-1-(6-fluoro-2-benzothiazolyl)ethylamine at a yield of 99.1% based on D-alanine-N-carboxy anhydride. After the completion of the reaction, 6 g of a 24% aqueous sodium hydroxide solution was added to make the pH of the mixture 10 or higher. The insoluble matter was removed by filtration. To the filtrate were added water and toluene for extraction. The resulting toluene layer was dried over anhydrous sodium sulfate and concentrated under vacuum, whereby 1.91 g (0.00973 mol) of (R)-1-(6-fluoro-2-benzothiazolyl)ethylamine was obtained. The isolated yield was 97.3% based on D-alanine-N-carboxy anhydride. The optical purity of the product was measured by high performance liquid chromatography using a chiral column, which was 99.8% e.e. Incidentally, the optical purity of the D-alanine used for synthesis of the D-alanine-N-carboxy anhydride was 99.8% e.e.

EXAMPLE 2

An operation was conducted in the same manner as in Example 1 except that 30 ml of N,N-dimethylacetamide was replaced by 50 ml of N,N-dimethylformamide. After the completion of the operation, the reaction mixture was subjected to high performance liquid chromatography analysis using an absolute calibration method, which indicated formation of (R)-1-(6-fluoro-2-benzothiazolyl)ethylamine at a yield of 95.8% based on D-alanine-N-carboxy anhydride. A post-treatment was conducted in the same manner as in Example 1 to obtain 1.85 g (0.00942 mol) of (R)-1-(6-fluoro-2-benzothiazolyl)ethylamine. The isolated yield was 94.2%.

EXAMPLE 3

An operation was conducted in the same manner as in Example 1 except that 30 ml of N,N-dimethylacetamide was replaced by 15 ml of 1-methyl-2-pyrrolidone. After the completion of the operation, the reaction mixture was subjected to high performance liquid chromatography analysis using an absolute calibration method, which indicated formation of (R)-1-(6-fluoro-2-benzothiazolyl)ethylamine in 92.9% yield based on D-alanine-N-carboxy anhydride. A post-treatment was conducted in the same manner as in Example 1 to obtain 1.80 g (0.00915 mol) of (R)-1-(6-fluoro-2-benzothiazolyl)ethylamine. The isolated yield was 91.5%.

EXAMPLE 4

An operation was conducted in the same manner as in Example 1 except that 30 ml of N,N-dimethylacetamide was replaced by 20 ml of 1,3-dimethyl-3,4,5,6-tetrahydro-2(1H) pyrimidinone. After the completion of the operation, the reaction mixture was subjected to high performance liquid chromatography analysis using an absolute calibration method, which indicated formation of (R)-1-(6-fluoro-2-benzothiazolyl)ethylamine in 96.1% yield based on D-alanine-N-carboxy anhydride.

EXAMPLE 5

An operation was conducted in the same manner as in Example 1 except that 1.14 g (0.01 mol) of D-alanine-N-carboxy anhydride was replaced by 1.01 g (0.01 mol) of glycine-N-carboxy anhydride. A post-treatment was conducted in the same manner as in Example 1 to obtain 1.67 g (0.00916 mol) of (6-fluoro-2-benzothiazolyl) methylamine. The isolated yield was 91.6% based on glycine-N-carboxy anhydride.

EXAMPLE 6

An operation was conducted in the same manner as in Example 1 except that 1.75 g (0.005 mol) of bis(5-fluoro-2-aminothiophenol) zinc salt was replaced by 1.71 g (0.005 mol) of bis(3-methyl-2-aminothiophenol) zinc salt. A post-treatment was conducted in the same manner as in Example 1 to obtain 1.81 g (0.00941 mol) of (R)-1-(4-methyl-2-benzothiazolyl)ethylamine. The isolated yield was 94.1% based on D-alanine-N-carboxy anhydride. The optical purity of the product was measured by high performance liquid chromatography using a chiral column, which was 99.8% e.e. Incidentally, the optical purity of the D-alanine used for synthesis of the D-alanine-N-carboxy anhydride was 99.8% e.e.

EXAMPLE 7

An operation was conducted in the same manner as in Example 1 except that 1.75 g (0.005 mol) of bis(5-fluoro-2-aminothiophenol) zinc salt was replaced by 1.71 g (0.005 mol) of bis(3-methyl-2-aminothiophenol) zinc salt and 1.14 g (0.01 mol) of D-alanine-N-carboxy anhydride was replaced by 1.01 g (0.01 mol) of glycine-N-carboxy anhydride. A post-treatment was conducted in the same manner as in Example 1 to obtain 1.05 g (0.00929 mol) of (4-methyl-2-benzothiazolyl)methylamine. The isolated yield was 92.9% based on glycine-N-carboxy anhydride.

EXAMPLE 8

An operation was conducted in the same manner as in Example 1 except that 1.14 g (0.01 mol) of D-alanine-N-carboxy anhydride was replaced by 1.42 g (0.01 mol) of L-valine-N-carboxy anhydride. A post-treatment was conducted in the same manner as in Example 1 to obtain 2.15 g (0.00956 mol) of (S)-1-(6-fluoro-2-benzothiazolyl)-2-methylpropylamine. The isolated yield was 95.6% based on L-valine-N-carboxy anhydride. The optical purity of the product was measured by high performance liquid chromatography using a chiral column, which was 99.7% e.e. Incidentally, the optical purity of the L-valine used for synthesis of the L-valine-N-carboxy anhydride was 99.7% e.e.

EXAMPLE 9

An operation was conducted in the same manner as in Example 1 except that 1.14 g (0.01 mol) of D-alanine-N-carboxy anhydride was replaced by 1.42 g (0.01 mol) of L-valine-N-carboxy anhydride and 1.75 g (0.005 mol) of bis(5-fluoro-2-aminothiophenol) zinc salt was replaced by 1.71 g (0.005 mol) of bis(3-methyl-2-aminothiophenol) zinc salt. A post-treatment was conducted in the same manner as in Example 1 to obtain 2.07 g (0.00941 mol) of (S)-1-(4-methyl-2-benzothiazolyl)-2-methylpropylamine. The isolated yield was 94.1% based on L-valine-N-carboxy anhydride.

EXAMPLE 10

An operation was conducted in the same manner as in Example 1 except that 1.75 g (0.005 mol) of bis(5-fluoro-2-aminothiophenol) zinc salt was replaced by 1.74 g (0.005 mol) of bis(5-fluoro-2-aminothiophenol) copper salt and 30 ml of N,N-dimethylacetamide was replaced by 30 ml of 1-methyl-2-pyrrolidone. After the completion of the operation, the reaction mixture was subjected to high performance liquid chromatography analysis using an absolute calibration method, which indicated formation of (R)-1-(6-fluoro-2-benzothiazolyl)ethylamine at a yield of 62.5% based on D-alanine-N-carboxy anhydride.

EXAMPLE 11

An operation was conducted in the same manner as in Example 1 except that the reaction of 1.75 g (0.005 mol) of bis(5-fluoro-2-aminothiophenol) zinc salt with 1.14 g (0.01 mol) of D-alanine-N-carboxy anhydride was conducted at 0° C. After the completion of the operation, the reaction mixture was subjected to high performance liquid chromatography analysis using an absolute calibration method, which indicated formation of (R)-1-(6-fluoro-2-benzothiazolyl)ethylamine at a yield of 72.0% based on D-alanine-N-carboxy anhydride.

EXAMPLE 12

An operation was conducted in the same manner as in Example 1 except that the reaction of 1.75 g (0.005 mol) of bis(5-fluoro-2-aminothiophenol) zinc salt with 1.14 g (0.01 mol) of D-alanine-N-carboxy anhydride was conducted at −30° C. After the completion of the operation, the reaction mixture was subjected to high performance liquid chromatography analysis using an absolute calibration method, which indicated formation of (R)-1-(6-fluoro-2-benzothiazolyl)ethylamine at a yield of 95.7% based on D-alanine-N-carboxy anhydride.

EXAMPLE 13

A mixture of 69 g (0.197 mol) of bis(5-fluoro-2-aminothiophenol) zinc salt and 700 ml of N,N-dimethylacetamide was cooled to −10° C. Thereto was added 40 g (0.347 mol) of D-alanine-N-carboxy anhydride. The mixture was stirred at −10° C. for 3 hours. While the internal temperature was maintained at 30° C. or below, 126 g (0.662 mol) of p-toluenesulfonic acid monohydrate was added in small portions. After the reaction mixture was stirred at room temperature for 1 hour, water and N,N-dimethylacetamide was removed under vacuum at 80° C. or below. To the residue were added 700 ml of hot water and 74 g (0.389 mol) of p-toluenesulfonic acid monohydrate, and the mixture was heated at reflux until the solid was dissolved completely to obtain a homogeneous solution. The solution was allowed to stand and cool to room temperature, whereby (R)-1-(6-fluoro-2-benzothiazolyl)ethylamine p-toluenesulfonate was precipitated as white crystals. The crystals were collected by filtration and dried. The yield was 95 g (yield: 70%).

Melting point: 242° C. (decomposed)

$[\alpha]_D^{25}$=+7.09 (CH$_3$OH, c=1.03)

The above-obtained (R)-1-(6-fluoro-2-benzothiazolyl)ethylamine p-toluenesulfonate was reacted with an aqueous sodium hydroxide solution for amine liberation, and the reaction mixture was subjected to high performance liquid chromatography (optically active column=Chiral Cell OD, produced by Daicel Chemical Industries, ltd.). As a result, the optical purity of liberated (R)-1-(6-fluoro-2-benzothiazolyl)ethylamine was 98% e.e.

EXAMPLE 14

In 400 ml of N,N-dimethylacetamide, 28.8 g (0.082 mol) of bis(5-fluoro-2-aminothiophenol) zinc salt was dissolved. The solution was cooled to –10° C. Thereto was added 24.5 g (0.213 mol) of L-alanine-N-carboxy anhydride. The mixture was stirred at –10° C. for 3 hours. Thereto was added 72.3 g (0.380 mol) of p-toluenesulfonic acid monohydrate. The mixture was stirred at room temperature for 1 hour. Then, while the mixture was maintained at 80° C. or below, the mixture was concentrated under vacuum. To the residue was added a solution of 4 g (0.021 mol) of p-toluenesulfonic acid monohydrate dissolved in 200 ml of hot water. The mixture was heated with stirring until the solid was dissolved completely. When the reaction content became a homogeneous solution, the heating was stopped and the reaction mixture was cooled to room temperature. As a result, (S)-1-(6-fluoro-2-benzothiazolyl)ethylamine p-toluenesulfonate was precipitated as white crystals. The crystals were collected by filtration and dried. The yield was 52.5 g (yield: 88.6%).

Melting point: 242° C. (decomposed)

$[\alpha]_D^{25}$=–6.85 (CH$_3$OH, c=1.007)

The above-obtained (S)-1-(6-fluoro-2-benzothiazolyl)ethylamine p-toluenesulfonate was reacted with an aqueous sodium hydroxide solution for amine liberation, and the reaction mixture was subjected to high performance liquid chromatography (optically active column=Chiral Cell OD, produced by Daicel Chemical Industries, ltd.). As a result, the optical purity of liberated (S)-1-(6-fluoro-2-benzothiazolyl)ethylamine was 99.7% e.e.

COMPARATIVE REFERENCE EXAMPLE 1

To 50 ml of chlorobenzene were added 1.75 g (0.005 mol) of bis(5-fluoro-2-aminothiophenol) zinc salt and 0.32 g (0.001 mol) of tetrabutylammonium bromide. The mixture was cooled to 0° C. in a nitrogen current. Thereto was added, at the same temperature, 1.14 g (0.01 mol) of D-alanine-N-carboxy anhydride. The mixture was stirred at 0° C. for 3 hours. Then, 18 g of a 5% aqueous hydrochloric acid solution was dropwise added at 5° C. or below. After the completion of the dropwise addition, the mixture was stirred at 5° C. or below for 1 hour. High performance liquid chromatography analysis using an absolute calibration method of the reaction mixture was conducted, which indicated formation of (R)-1-(6-fluoro-2-benzothiazolyl)ethylamine at a yield of 8.3% based on D-alanine-N-carboxy anhydride.

COMPARATIVE REFERENCE EXAMPLE 2

To 50 ml of chlorobenzene were added 1.75 g (0.005 mol) of bis(5-fluoro-2-aminothiophenol) zinc salt, 0.32 g (0.001 mol) of tetrabutylammonium bromide and 1.20 g (0.02 mol) of acetic acid. The mixture was cooled to 0° C. in a nitrogen current. Thereto was added, at the same temperature, 1.14 g (0.01 mol) of D-alanine-N-carboxy anhydride. The mixture was stirred at 0° C. for 3 hours. Then, 18 g of a 5% aqueous hydrochloric acid solution was dropwise added at 5° C. or below. After the completion of the dropwise addition, the mixture was stirred at 5° C. or below for 1 hour. High performance liquid chromatography analysis using an absolute calibration method of the reaction mixture was conducted, which indicated formation of (R)-1-(6-fluoro-2-benzothiazolyl)ethylamine at a yield of 31.4% based on D-alanine-N-carboxy anhydride.

REFERENCE EXAMPLE 1

In 500 ml of toluene, 18.9 g (0.093 mol) of N-isopropoxycarbonyl-L-valine was dissolved. The solution was cooled to –5° C. Thereto were dropwise added, at –5° C., 23.0 g (0.233 mol) of N-methylmorpholine and 12.7 g (0.093 mol) of isobutyl chlorocarbonate. Thereto was added, at –5° C., 17.4 g (0.047 mol) of (R)-1-(6-fluoro-2-benzothiazolyl)ethylamine p-toluenesulfonate in one portion. The mixture was stirred at the same temperature for 0.5 hour and then at room temperature for 2 hours. To the reaction mixture was added 300 ml of water. The mixture was heated to 70° C. to dissolve the solid. The toluene layer was separated, washed with hot water, and then cooled, whereby a solid was precipitated. The solid was collected by filtration and dried to obtain 23.7 g (yield: 70%) of isopropyl {(S)-1-[(R)-1-(6-fluorobenzothiazol-2-yl)ethylcarbamoyl]-2-methylpropyl}carbamate. The compound obtained was confirmed for the structure by IR analysis and NMR analysis in comparison with its authentic material and identified.

Melting point: 172 to 173° C.

Purity: 99.7% (high performance liquid chromatography)

Optical purity: 99.6% d.e.

REFERENCE EXAMPLE 2

In 500 ml of toluene, 10.2 g (0.05 mol) of N-isopropoxycarbonyl-D-valine was dissolved. Thereto were dropwise added, at –5° C., 12.4 g (0.0125 mol) of N-methylmorpholine and 6.8 g (0.05 mol) of isobutyl chlorocarbonate. Thereto was added, at –5° C., 18.3 g (0.05 mol) of (R)-1-(6-fluoro-2-benzothiazolyl)ethylamine p-toluenesulfonate. A reaction and a post-treatment were conducted in the same manner as in Reference Example 1, and the suspension of a solid in toluene was filtered to collect the solid. The solid was subjected to Soxhlet extraction for 1 week, and the extract was concentrated to obtain a solid. The solid was recrystallized from xylene to obtain 11.6 g (yield: 62.7%) of isopropyl {(R)-1-[(R)-1-(6-fluorobenzothiazol-2-yl)ethylcarbamoyl]-2-methylpropyl}carbamate. The compound obtained was confirmed for the structure by IR analysis and NMR analysis in comparison with its authentic material and identified.

Melting point: 244 to 246° C.
Purity: 99.5% (high performance liquid chromatography)
Optical purity: 99.2% d.e.

REFERENCE EXAMPLE 3

In 250 ml of toluene, 13.4 g (0.066 mol) of N-isopropoxycarbonyl-L-valine was dissolved. Thereto was added 14.3 g (0.144 mol) of N-methylmorpholine. Then was dropwise added at −10° C., 8.6 g (0.063 mol) of isobutyl chlorocarbonate. Thereto was added 22 g (0.06 mol) of (S)-1-(6-fluoro-2-benzothiazolyl)ethylamine p-toluenesulfonate. A reaction and a post-treatment were conducted in the same manner as in Reference Example 1, and the suspension of a solid in toluene was filtered at 70° C. to collect the solid. The solid was washed with water and toluene and dried to obtain 18.5 g (yield: 81.1%) of isopropyl {(S)-1-[(S)-1-(6-fluorobenzothiazol-2-yl)ethylcarbamoyl]-2-methylpropyl}carbamate. The compound obtained was confirmed for the structure by IR analysis and NMR analysis in comparison with its authentic material and identified.

Melting point: 242 to 245° C.
Purity: 99.4% (high performance liquid chromatography)
Optical purity: 99.5% d.e.

REFERENCE EXAMPLE 4

In 250 ml of toluene, 13.4 g (0.066 mol) of N-isopropoxycarbonyl-D-valine was dissolved. Thereto was added 14.3 g (0.144 mol) of N-methylmorpholine. Then was dropwise added at −10° C., 8.6 g (0.063 mol) of isobutyl chlorocarbonate. Thereto was added 22 g (0.06 mol) of (S)-1-(6-fluoro-2-benzothiazolyl)ethylamine p-toluenesulfonate. A reaction and a post-treatment were conducted in the same manner as in Reference Example 1, and the hot toluene solution was filtered in a hot state to remove the insoluble matter. The filtrate was cooled, whereby crystals were precipitated. The crystals were collected by filtration and dried to obtain 15.8 g (yield: 69.3%) of isopropyl {(R)-1-[(S)-1-(6-fluorobenzothiazol-2-yl)ethylcarbamoyl]-2-methylpropyl}carbamate. The compound obtained was confirmed for the structure by IR analysis and NMR analysis in comparison with its authentic material and identified.

Melting point: 179 to 180° C.
Purity: 100% (high performance liquid chromatography)
Optical purity: 100% d.e.

Industrial Applicability

According to the present invention, there is provided an industrial process for producing, from a 2-aminothiophenol derivative, a substituted alkylamine [ typified by a 1-(2-benzothiazolyl)alkylamine] or a salt thereof at a high yield in high handleability. In the present process, even when the intended substituted alkylamine is an optically active compound, the intended product can be produced without reducing the optical purity of the optically active raw material used.

According to the present invention, there is also provided a substituted alkylamine salt which is useful for production of an intermediate for a fungicide for agriculture or horticulture (see JP-A-8-176115) and which is easily crystallized and stable, for example, a 1-(6-halogeno-2-benzothiazolyl)ethylamine p-toluenesulfonate.

What is claimed is:

1. A process for producing a substituted alkylamine represented by formula (3):

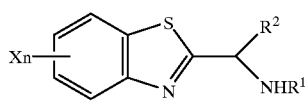

(wherein X is a hydrogen atom, a halogen atom, an alkyl group, an alkoxy group, a cyano group or a nitro group; n is an integer of 1 to 4; and $R^1$ and $R^2$ are each independently a hydrogen atom or an alkyl group which may be substituted with phenyl group, and may together form a 5- or 6-membered ring) or a salt thereof, which process comprises reacting a 2-aminothiophenol derivative metal salt represented by formula (1):

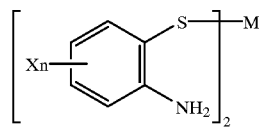

(wherein M is a bivalent metal atom; X has the same definition as given above; and n has the same definition as given above) with an amino acid-N-carboxy anhydride represented by formula (2):

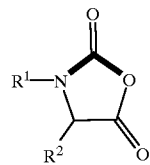

(wherein $R^1$ and $R^2$ have the same definitions as given above) and then subjecting the reaction product to cyclization under an acidic condition.

2. A process for producing a substituted alkylamine or a salt thereof according to claim 1, wherein the reaction of the 2-aminothiophenol derivative metal salt represented by formula (1) with the amino acid-N-carboxy anhydride represented by formula (2) is conducted in an amide type aprotic polar solvent.

3. A process for producing a substituted alkylamine or a salt thereof according to claim 1, wherein the 2-aminothiophenol derivative metal salt represented by formula (1) is a salt of a Ib or IIb group metal.

4. A process for producing a substituted alkylamine or a salt thereof according to claim 3, wherein the 2-aminothiophenol derivative metal salt represented by formula (1) is a zinc salt.

5. A process for producing a substituted alkylamine or a salt thereof according to claim 1, wherein the amino acid-N-carboxy anhydride represented by the formula (2) is DL-alanine-N-carboxy anhydride, D-alanine-N-carboxy anhydride or L-alanine-N-carboxy anhydride.

6. A process for producing a substituted alkylamine or a salt thereof according to claim 1, wherein the reaction of the 2-aminothiophenol derivative metal salt represented by formula (1) with the amino acid-N-carboxy anhydride represented by formula (2) is conducted in a temperature range of −50 to 60° C.

7. A process for producing a substituted alkylamine or a salt thereof according to claim 1, wherein the reaction of the 2-aminothiophenol derivative metal salt represented by formula (1) with the amino acid-N-carboxy anhydride represented by formula (2) is conducted in a temperature range of −30 to 10° C.

8. A (substituted) benzenesulfonic acid salt of a 1-(6-halogeno-2-benzothiazolyl)ethylamine represented by the following formula:

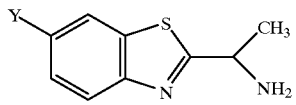

(wherein Y is a halogen atom).

9. A (substituted) benzenesulfonic acid salt according to claim 8, wherein the (substituted) benzenesulfonic acid is p-toluenesulfonic acid.

10. A (substituted) benzenesulfonic acid salt according to claim 8, wherein Y is a fluorine atom.

11. A process for producing a substituted alkylamine or a salt thereof according to claim 2, wherein the 2-aminothiophenol derivative metal salt represented by formula (1) is a salt of a Ib or IIb group metal.

12. A process for producing a substituted alkylamine or a salt thereof according to claim 11, wherein the 2-aminothiophenol derivative metal salt represented by formula (1) is a zinc salt.

13. A process for producing a substituted alkylamine or a salt thereof according to claim 2, wherein the amino acid-N-carboxy anhydride represented by formula (2) is DL-alanine-N-carboxy anhydride, D-alanine-N-carboxy anhydride or L-alanine-N-carboxy anhydride.

14. A process for producing a substituted alkylamine or a salt thereof according to claim 2, wherein the reaction of the 2-aminothiophenol derivative meta salt represented by formula (1) with the amino acid-N-carboxy anhydride represented by formula (2) is conducted in a temperature range of −50 to 50° C.

15. A process for producing a substituted alkylamine or a salt thereof according to claim 2, wherein the reaction of the 2-aminothiophenol derivative metal salt represented by formula (1) with the amino acid-N-carboxy anhydride represented by formula (2) is conducted in a temperature range of −30 to 10° C.

16. A (substituted) benzenesulfonic acid salt according to claim 9, wherein Y is a fluorine atom.

* * * * *